US009969661B2

(12) United States Patent
Han et al.

(10) Patent No.: US 9,969,661 B2
(45) Date of Patent: May 15, 2018

(54) METHOD OF PREPARING CONJUGATED DIENE AND DEVICE THEREFOR

(71) Applicant: LG CHEM, LTD., Seoul (KR)

(72) Inventors: Sang Jin Han, Daejeon (KR); Jun Han Kang, Daejeon (KR); Dong Hyun Ko, Daejeon (KR); Hyun Seok Nam, Daejeon (KR); Joo Hyuck Lee, Daejeon (KR); Jun Kyu Han, Daejeon (KR); Myung Ji Suh, Daejeon (KR); Kyong Yong Cha, Daejeon (KR); Dae Heung Choi, Daejeon (KR); Ye Seul Hwang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days. days.

(21) Appl. No.: 15/021,611

(22) PCT Filed: Oct. 20, 2015

(86) PCT No.: PCT/KR2015/011061
§ 371 (c)(1),
(2) Date: Mar. 11, 2016

(87) PCT Pub. No.: WO2016/153139
PCT Pub. Date: Sep. 29, 2016

(65) Prior Publication Data
US 2017/0036972 A1 Feb. 9, 2017

(30) Foreign Application Priority Data
Mar. 24, 2015 (KR) .................. 10-2015-0040468

(51) Int. Cl.
C07C 5/48 (2006.01)
C07C 5/42 (2006.01)
(Continued)

(52) U.S. Cl.
CPC ................... C07C 5/48 (2013.01); B01J 3/00 (2013.01); C07C 5/3332 (2013.01); C07C 5/42 (2013.01); C07C 7/005 (2013.01); C07C 7/05 (2013.01)

(58) Field of Classification Search
CPC ................ C07C 5/48; C07C 5/42; C07C 7/05
See application file for complete search history.

(56) References Cited

U.S. PATENT DOCUMENTS 3,496,224 A * 2/1970 Ayers .................... C07C 303/42
510/495
3,557,238 A * 1/1971 Cunningham ............ C07C 5/48
502/51
(Continued)

FOREIGN PATENT DOCUMENTS

CN 104418420 A 3/2015
JP S61-005030 1/1986
(Continued)

Primary Examiner — In Suk C Bullock
Assistant Examiner — Youngsul Jeong
(74) Attorney, Agent, or Firm — Dentons US LLP

(57) ABSTRACT

Disclosed are a method of preparing conjugated diene and a device therefor. More particularly, disclosed a method of preparing conjugated diene, wherein generated gas including butadiene is cooled and then water discharged at a lower part is not directly treated as waste water and subjected to byproduct removal and steam-extraction to utilize converted steam, and an installation issue of an existing biological waste water disposal equipment due to an excessive amount of byproducts can be resolved, and a device therefor are disclosed.

6 Claims, 1 Drawing Sheet

(51) Int. Cl.
*C07C 7/00* (2006.01)
*C07C 7/05* (2006.01)
*C07C 5/333* (2006.01)
*B01J 3/00* (2006.01)

(56) References Cited

U.S. PATENT DOCUMENTS

2004/0200381 A1   10/2004   Zatterqvist
2014/0200381 A1*  7/2014    Josch .................... C07C 7/05
                                                    585/621

FOREIGN PATENT DOCUMENTS

| JP | S61-5030 A | 1/1986 | | |
|---|---|---|---|---|
| KR | 10-2007-0011280 A | 1/2007 | | |
| KR | 10-2007-0095335 A | 9/2007 | | |
| KR | 10-2013-0036470 | 4/2013 | | |
| KR | 10-2013-0036470 A | 4/2013 | | |
| KR | 1020130036470 | * 4/2013 | ............. | C07C 5/333 |

* cited by examiner

METHOD OF PREPARING CONJUGATED DIENE AND DEVICE THEREFOR

CROSS-REFERENCE TO RELATED APPLICATIONS

This application is a National Stage Application of International Application No. PCT/KR2015/011061, filed on Oct. 20, 2015, which claims the benefit of Korean Patent Application No. 10-2015-0040468, filed on Mar. 24, 2015, all of which are hereby incorporated by reference in their entirety for all purposes as if fully set forth herein.

TECHNICAL FIELD

The present invention relates to a method of preparing conjugated diene and a device therefor. More particularly, the present invention relates to a method of preparing conjugated diene, wherein generated gas including butadiene is cooled and then water discharged at a lower part is not directly treated as waste water and subjected to byproduct removal and steam-extraction to utilize converted steam, and an installation issue of an existing biological waste water disposal equipment due to an excessive amount of byproducts can be resolved, and a device therefor.

BACKGROUND ART 1,3-butadiene can be prepared by performing contact oxidative dehydrogenation for monoolefins, such as n-butene, in the presence of a catalyst.

U.S. Pat. No. 4,595,788, which is an example of existing technologies of collecting hydrocarbon containing butadiene from a reactive gas mixture including 1,3-butadiene generated by contact oxidative dehydrogenation, discloses a technology of absorbing most of a $C_4$ ingredient including butadiene before isolation of crude butadiene, and degassing remaining gas and then circulating the same in a reactor.

In accordance this technology, a portion of a light byproduct (light carbonyl, compound having boiling point of 100° C. or less and carbon number of 4) included in the generated gas and most of a heavy byproduct (heavy carbonyl, compound having boiling point of 100° C. or less and carbon number of 5 or 6) are removed by being absorbed into a cooling tower. However, most of the light byproduct and the portion of the heavy byproduct are subjected to a stripping process performed as a subsequent process. Accordingly, after the stripping, the light and heavy byproducts should be subjected to post-treatment, and some of the light byproduct may react with the butadiene included in the generated gas to function as a cause of butadiene loss. In addition, a general biological waste water disposal equipment required due to an excessive content of byproducts contained in water discharged from the cooling tower is a heavy burden. Accordingly, there was an attempt to feed an aqueous alkaline solution, fresh water, etc., as a cooling solvent, into the cooling tower such that an excessive content of byproducts in water discharged from the cooling tower is reduced. However, slurry was formed and fouling was generated due to a solid-phase salt and a heave material with a boiling point of 100° C. or more, which are generated upon feeding of the aqueous alkaline solution. In addition, the amount of waste water greatly increased upon feeding of the fresh water.

Therefore, there is an urgent need for technology of treating water discharged from the cooling tower while increasing process efficiency.

DISCLOSURE

Technical Problem

Therefore, the present invention has been made in view of the above problems, and it is one object of the present invention to provide a method of preparing conjugated diene, wherein generated gas including butadiene is cooled and then water discharged at a lower part is not directly treated as waste water and subjected to byproduct removal and steam-extraction to utilize converted steam, and an installation issue of an existing biological waste water disposal equipment due to an excessive amount of byproducts can be resolved, and a device therefor.

The above and other objects can be accomplished by the present invention described below.

Technical Solution

In accordance with one aspect of the present invention, provided is a method of preparing conjugated diene, wherein the method includes a) oxidation-dehydrogenating raw material gas including n-butene in the presence of a catalyst to generate gas including butadiene; b) contacting the generated gas with cooling water to cool; c) preparing an organic solution by allowing the cooled generated gas to be absorbed into an organic solvent; and d) stripping the organic solution to obtain crude butadiene, wherein the contacting b) includes removing byproducts from discharged cooling water after contacting the generated gas with the cooling water, and then converting the byproduct-removed cooling water into steam and circulating the converted steam by means of an oxidative dehydrogenation reactor used in the oxidation-dehydrogenating a), wherein the amount of the converted steam is 50% by weight or more based on the discharged cooling water and the amount of a carbonyl compound is 1000 ppm or less.

In accordance with another aspect of the present invention, provided is a device for preparing conjugated diene including a reactor for oxidative dehydrogenation, a cooling tower, an absorption tower, a separation tower, and a device for treating lower-portion water discharged from the cooling tower including an equipment for removing a light byproduct, an equipment for precipitating a heavy byproduct, an equipment for extracting steam, and an equipment for treating waste water.

Advantageous Effects

As apparent from the fore-going, the present invention advantageously provides a method of preparing conjugated diene, wherein generated gas including butadiene is cooled and then water discharged at a lower part is not directly treated as waste water and subjected to byproduct removal and steam-extraction to utilize converted steam, and an installation issue of an existing biological waste water disposal equipment due to an excessive amount of byproducts can be resolved, and a device therefor.

BEST MODE

Now, the present invention will be described in more detail with reference to the following examples. These examples are provided only for illustration of the present invention and should not be construed as limiting the scope and spirit of the present invention.

A method of preparing conjugated diene according to the present invention includes a) oxidation-dehydrogenating raw material gas including n-butene in the presence of a catalyst to generate gas including butadiene; b) contacting the generated gas with cooling water to cool; c) preparing an organic solution by allowing the cooled generated gas to be absorbed into an organic solvent; and d) stripping the organic solution to obtain crude butadiene, wherein the contacting b) includes removing byproducts from discharged cooling water after contacting the generated gas with the cooling water, and then converting the byproduct-removed cooling water into steam and circulating the converted steam by means of an oxidative dehydrogenation reactor used in the oxidation-dehydrogenating a), wherein the amount of the converted steam is 50% by weight or more based on the discharged cooling water and the amount of a carbonyl compound is 1000 ppm or less.

The present invention advantageously provides a method of preparing conjugated diene, wherein generated gas including butadiene is cooled and then water discharged at a lower part is not directly treated as waste water and subjected to byproduct removal and steam-extraction to utilize converted steam, and an installation issue of an existing biological waste water disposal equipment due to an excessive amount of byproducts can be resolved.

The expression "byproducts" includes a light byproduct indicating a carbonyl compound such as aldehyde or ketone with a boiling point of 100° C. or less and a carbon number of 4 and a heavy byproduct indicating a carbonyl compound such as aldehyde or ketone with a boiling point of 100° C. or less and a carbon number of 5 or 6, unless otherwise specified.

The expression "steam" means vapor converted into water vapor after removal of byproducts from lower-portion discharged water of the cooling tower, unless otherwise specified.

Figure 2:
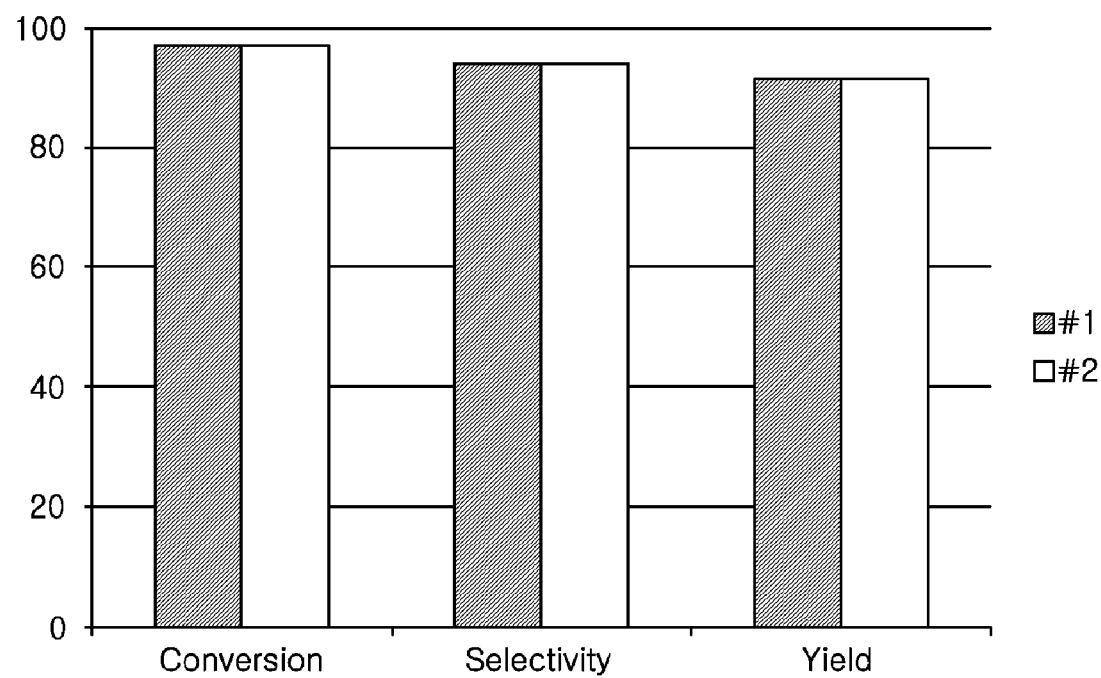
FIG. 2 is a graph comparing conversion rates, selectivity and yields of butadiene, which is one of generated gases discharged from the reactor for oxidation-dehydrogenating 1, of an experiment using fresh steam and an experiment using steam converted from a lower-portion discharged water at a cooling step according to the present invention, as vapor supplied into the reactor for oxidation-dehydrogenating 1 illustrated in FIG. 1.

In an embodiment, the amount of the converted steam may be 50% by weight or more, or 50 to 80% by weight based on the weight of the lower-portion discharged water. In addition, the converted steam may include byproducts in an amount of 1000 ppm or less, 918 ppm or less, or 496 ppm to 918 ppm. Within this range, when the steam is circulated through the oxidative dehydrogenation of step a), efficiency of the oxidative dehydrogenation of step a) may be maintained (See FIG. 2).

In an embodiment, when the byproducts are removed, a light byproduct removal process and a heavy byproduct precipitation process may be performed.

In an embodiment, the light byproduct removal process may be performed at 80° C. to 95° C. Within this range, the light byproduct may be effectively removed through an upper portion of a corresponding removal equipment. In an embodiment, the light byproduct removal process may be performed by means of a distillation column.

In an embodiment, in the heavy byproduct precipitation process, the heavy byproduct may be precipitated by adjusting pH to 11 or more, or 11 to 12 through addition of an alkaline substance.

In an embodiment, the alkaline substance may be NaOH, KOH, or an aqueous solution thereof.

In an embodiment, the heavy byproduct precipitation process may be performed using a neutralization tank.

The heavy byproduct precipitation process may, after precipitating byproducts, further include a filtration process.

In an embodiment, the steam may be prepared using a boiler.

As an embodiment, in the cooling of the step b), the cooling water is introduced into an upper portion of a cooling equipment, thus countercurrently contacting with the generated gas introduced into a lower part. A portion of used cooling water may be re-circulated and, in this case, process efficiency may be desirably enhanced.

In the present invention, discharged water remaining after being converted into the steam and collected byproducts may be treated through a separate waste water treatment process, particularly may be incinerated.

In an embodiment, a device for the preparation method may include, for example, a reactor for oxidative dehydrogenation, a cooling tower, an absorption tower, a separation tower, and a device for treating lower-portion water discharged from the cooling tower including an equipment for removing a light byproduct, an equipment for precipitating a heavy byproduct, an equipment for extracting steam, and an equipment for treating waste water. The device for treating discharged lower-portion water may further include an equipment for filtering a heavy byproduct between the equipment for precipitating a heavy byproduct and the equipment for extracting steam.

Figure 1:
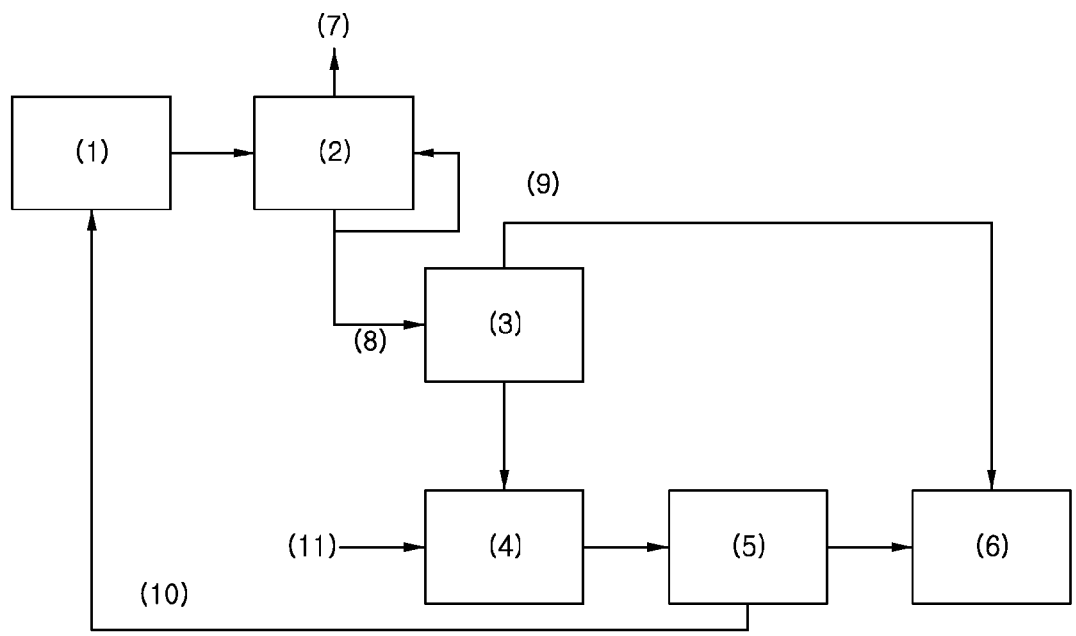
FIG. 1 is a flowchart mainly illustrating a process of treating lower-portion discharged water at a cooling step of a process of preparing butadiene.

Hereinafter, a method of converting cooling water, which is used to prepare conjugated diene, as steam according to the present invention, using a process for treating the cooled lower-portion discharged water and an equipment therefor is described in detail with reference to the accompanying figures. FIG. 1 below is a flowchart mainly illustrating the process of treating a lower-portion discharged water in a cooling step of a process of preparing butadiene.

First, a) a step of generating gas including butadiene by oxidation-dehydrogenating a raw material gas including n-butene in the presence of a catalyst is included.

The n-butene is 1-butene, 2-butene or a combination thereof.

In an embodiment, the raw material gas including n-butene may be high-purity n-butene gas, a fraction including, as a main ingredient, n-butene obtained by isolating butadiene and i-butene from a $C_4$ fraction being a byproduct of naphtha cracking, a butene fraction generated by dehydrogenation or oxidative dehydrogenation of N-butane, a reacted gas product obtained by dimerizing of ethylene, or gas including $C_4$ hydrocarbons obtained through fluid catalytic cracking of a heavy oil fraction.

In an embodiment, the raw material gas including n-butene may include n-butene in an amount of 40% by volume or more, preferably 60% by volume or more, more preferably 75% by volume or more, most preferably 99% by volume or more. Within this range, a reaction rate and a yield are superior.

In an embodiment, the catalyst may be a molybdenum-bismuth based catalyst.

The molybdenum-bismuth based catalyst is not specifically limited so long as it may be used in general oxidative dehydrogenation of butene.

In an embodiment, the molybdenum-bismuth based catalyst may be a composite oxide catalyst including molybdenum, bismuth, and cobalt.

In an embodiment, the oxidative dehydrogenation may be a reaction of preparing butadiene by reacting raw material gas including n-butene and gas containing oxygen molecules in the presence of a catalyst.

In an embodiment, the gas containing the oxygen molecules may contain oxygen molecules in an amount of 10 to 50% by volume, preferably 15 to 30% by volume, more preferably 20 to 25% by volume.

In an embodiment, the gas containing the oxygen molecules may include impurities such as nitrogen, argon, neon, and helium which do not greatly inhibit the oxidative dehydrogenation.

In another embodiment, the gas containing the oxygen molecules may be air.

In an embodiment, when the raw material gas and the gas containing the oxygen molecules are supplied into a reactor, the raw material gas and the gas containing the oxygen molecules are mixed and then a resultant mixed gas may be supplied to the reactor. A ratio of the raw material gas in the mixed gas may be, for example, 4.2 to 20.0% by volume.

In an embodiment, nitrogen gas and/or vapor may be supplied along with the mixed gas to the reactor. By feeding the nitrogen gas, the concentrations of combustible gas and oxygen may be controlled so that the mixed gas does not form detonating gas. In addition, by feeding the vapor, the concentrations of the combustible gas and the oxygen may be controlled and catalyst degradation may be suppressed.

When vapor is supplied to a reactor for oxidation-dehydrogenating 1, fresh vapor or vapor generated through an equipment for extracting steam 5 described below may be supplied. In an embodiment, the vapor may be in a volumetric ratio of 0.5 to 5.0 based on a supply amount of the raw material gas. When nitrogen gas is supplied to the reactor, the nitrogen gas may be supplied in a volumetric ratio of 0.5 to 8.0 based on a supply amount of the raw material gas.

The reactor used in the oxidative dehydrogenation is not specifically limited so long as it is a reactor generally used in the art. In an embodiment, the reactor may be a tubular reactor, a tank-type reactor, a fluidized bed reactor, or a fixed bed reactor.

The fixed bed reactor may be, for example, a multi-tubular reactor or a plate-type reactor.

The fixed bed reactor may include, for example, a catalyst layer to which a catalyst for the oxidative dehydrogenation is fixed. This catalyst layer may be composed of exclusively a catalyst or a solid that does not have reactivity to the catalyst. In addition, the catalyst layer may include the layer composed of exclusively the catalyst and the layer composed of the solid that does not have reactivity to the catalyst. Alternatively, the catalyst layer may include layers composed of exclusively the catalyst and layers composed of the solid that does not have reactivity to the catalyst.

When the solid or the layer containing the solid is included, it may be prevented that the temperature of the catalyst layer rapidly increases due to heat generated during reaction. In addition, when a plurality of catalyst layers are used, the catalyst layers may be formed in a layered structure from an inlet to an outlet, at which the generated gas is discharged, of the reactor.

When the catalyst layer includes the layer composed of the catalyst and a solid not having reactivity, a catalyst dilution rate represented by the following formula may be, for example, 10% to 99% by volume.

Dilution rate=[(Volume of solid)/(Volume of catalyst+Volume of solid)]×100

The solid not having reactivity is stable under a reaction condition to generate conjugated diene, and is not specifically limited so long as it does not have reactivity to raw materials such as monoolefin with a carbon atom number of 4 or more and products such as conjugated diene. For example, the solid may be a ceramic material such as alumina, zirconia, or the like, called inert ball.

The solid not having reactivity may have any one of a globular shape, a cylindrical shape, a ring shape, and an irregular shape. In addition, the size of the solid may be equal to that of the catalyst used in the present disclosure, and a particle size of the solid may be, for example, about 2 mm to 10 mm.

A filled length of the catalyst layer may be found by calculating material balance and heat balance when activity of a filled catalyst (activity of a diluted catalyst when dilution is performed using a solid not having reactivity), the size of the reactor, the temperature of a reactive raw material gas, reaction temperature, and a reaction condition are determined.

The oxidative dehydrogenation is a general exothermic reaction. In an embodiment, temperature for the oxidative dehydrogenation may be controlled to 250° C. to 450° C. and heating may be controlled with a heating medium (for example, dibenzyltoluene, nitrite, or the like).

When the reaction temperature, i.e., the temperature of the catalyst layer is higher than 450° C., catalytic activity may be rapidly decreased as the reaction is continued. When the temperature of the catalyst layer is less than 250° C., the yield of a targeted product, i.e., the conjugated diene, tends to be decreased.

The interior pressure of the reactor may be, for example, 0 MPaG or more, or higher than 0 MPaG and 0.5 MPaG or less. Residence time in the reactor may be 0.36 to 72 seconds. In addition, a ratio of the discharge of the mixed gas to the amount of the catalyst in the reactor may be 50 $h^{-1}$ to 10000 $h^{-1}$.

Although a discharge difference between an inlet and an outlet of the reactor depends upon the discharge of the raw material gas at the reactor inlet and the discharge of the generated gas at the reactor outlet, a ratio of the discharge at the outlet to the discharge at the inlet may be, for example, 100 to 110% by volume. Through oxidative dehydrogenation of the monoolefin in the raw material gas, conjugated diene corresponding to the monoolefin is generated and thus gas containing the conjugated diene is obtained at the outlet of the reactor. Although the concentration of the conjugated diene, which corresponds to the monoolefin, among raw material gases contained in the obtained gas depends upon the concentration of the monoolefin contained in the raw material gas, the concentration of the conjugated diene may be 1 to 15% by volume and the concentration of unreacted monoolefin may be 0 to 7% by volume.

Heavy by-products contained in the generated gas may be different depending upon the types of impurities contained in the raw material gas. The heavy by-products may be included in an amount of 0.05 to 0.10% by volume in a reactive gas.

In order to isolate butadiene from generated gas including butadiene prepared through oxidative dehydrogenation from the reactor for oxidation-dehydrogenating 1 illustrated in FIG. 1, a cooling equipment 2, a solvent absorption process (not shown), an isolation process (not shown), a purification process (not shown), and the like may be included.

In particular, the generated gas including butadiene prepared through oxidative dehydrogenation is supplied to the cooling equipment 2 (quencher) and cooled at step b), and then vapor containing discharged butadiene discharged to an upper part of the cooling equipment 2, i.e., the generated gas cooled 7, is absorbed into an organic solvent to prepare an organic solution, i.e., an absorption solution.

The cooling water is introduced into an upper part of the cooling equipment 2 via a pipe and countercurrently contacts the generated gas introduced into a lower part of the cooling equipment 2. The cooling water cooling generated gas by such countercurrent contact is discharged via a pipe of the bottom of the cooling equipment 2.

In an embodiment, the cooling may be performed at 5 to 100° C., or 30 to 70° C.

In an embodiment, the cooling may be performed by means of an equipment generally called quencher. As a specific embodiment, in the cooling, water at 30° C. to 50° C., or 35° C. to 45° C. is sprayed to an upper part of the cooling tower to be condensed. In addition, discharged water at a lower part of the cooling tower is cooled and re-circulated.

Lower-portion water discharged through a pipe at a lower part of the cooling tower is fed into an equipment for removing a light byproduct 3 via the transfer line 8 and operation is performed at 80° C. to 95° C. Accordingly, the light byproduct is discharged through an upper part of the equipment for removing a light byproduct 3 and transferred to the equipment for treating waste water 6 via a transfer line 9, following treatment.

Remaining water discharged through a lower part of the equipment for removing a light byproduct 3 is transferred to an equipment for precipitating a heavy byproduct 4. Subsequently, an alkaline substance such as NaOH or KOH or an aqueous solution thereof is fed via an alkaline substance feed line 11, and operation is performed at pH 11 or higher to more to extract steam by passing through an equipment for extracting steam 5 (boiler) in a state in which a heavy byproduct is precipitated. Converted steam is re-circulated in the reactor for oxidation-dehydrogenating 1 of step a) via a steam transfer line 10.

A discharged water remainder from which steam is extracted and byproducts are removed is transferred to the equipment for treating waste water 6, followed by being condensed and treated as waste water.

A process of isolating butadiene from gas discharged through an upper part of the cooling tower is described below.

The cooled generated gas is discharged through the top of the cooling tower and then pressed under a predetermined pressure via a compressor, followed by being supplied to an absorption tower (absorber) to contact with an organic solvent.

In an embodiment, the absorption solvent may be saturated $C_6$ to $C_{10}$ hydrocarbon, aromatic $C_6$ to $C_8$ hydrocarbons, or an amide based compound. In a specific embodiment, the absorption solvent may be dimethyl formamide (DMF).

The absorption solvent absorbs butadiene, non-reactive raw material gas, etc. among generated gases. Here, gas ingredients not absorbed into the absorption solvent is discharged through the top of the absorption tower to be combusted (off gas) or is re-sent to the reactor and circulated.

In addition, a solution absorbing the generated gas including butadiene and the non-reactive raw material gas, i.e., the organic solution, is discharged through the bottom of the absorption tower and supplied to an upper part of the degassing tower (degasser) via a pipe.

In an embodiment, the absorption solution of the generated gas prepared in the absorption step is sprayed to an upper part of the degassing tower before being subjected to a stripping process, thereby being subjected to a degassing process. In this case, nitrogen, oxygen, etc. dissolved in the absorption solution may be removed.

Since small amounts of nitrogen and oxygen are dissolved in the absorption solution of the generated gas obtained from the absorption tower, the absorption solution of the generated gas is supplied to the degassing tower and heated, thereby being gasficated and removed. In this case, since a portion of butadiene or raw material gas is gasficated in some cases, gas discharged through the top of the degassing tower is circulated near an inlet of the compressor in order to increase a recovery rate of the butadiene.

As needed, the generated gas discharged from the top of the cooling tower (quencher) passes through a cooler before being entered into the compressor, whereby condensate is isolated from the generated gas. In addition, the generated gas with elevated pressure after being entered into the compressor passes through a dehydration tower filled with a drying material such as molecular sieve, etc. before being entered into the absorption tower.

The stripping is not specifically limited so long as the crude butadiene and the solvent may be separated.

In an embodiment, the stripping may be performed by distillation separation.

In a particular embodiment, the distillation separation may be a method of extracting crude butadiene from the top of the tower by distilling the absorption solution of the generated gas by means of a reboiler and a condenser.

In an embodiment, the organic solution, from which remaining gas is removed through the degassing, is cooled to 10 to 30° C. and then sprayed to an upper part of a tower for separating a solvent.

The non-purified crude butadiene and the separated solvent may be re-used as an organic solvent of the absorption tower.

Now, the present invention will be described in more detail with reference to the following examples. These examples are provided only for illustration of the present invention and should not be construed as limiting the scope and spirit of the present invention.

EXAMPLE

Example 1 and Comparative Example 1

Example 1 and Comparative Example 1 were carried out in order to examine the content of byproducts (carbonyl) included in steam per operation condition of the equipment for precipitating a heavy byproduct 4 next to an equipment for precipitating a light byproduct 3 and determine whether discharged water was properly treated.

Example 1

Referring to FIG. 1, oxidative dehydrogenation was carried out using steam in a reactor for oxidation-dehydrogenating 1 filled with a bismuth-molybdenum based catalyst (in a mole ratio, Mo:Bi:Fe:Co:K:Cs=1 to 15:1 to 10:1 to 10:1 to 10:0.01 to 1.5:greater than 0 and 1.5 or less) under conditions of 320° C., a space velocity of 75 $h^{-1}$, and, oxygen/butene:steam/butene:nitrogen/butene=1:4:12 in a mole ratio.

Gas containing butadiene obtained by the oxidative dehydrogenation was introduced into a lower part of the cooling tower 2 (quencher) and, at the same time, the generated gas was cooled to 100° C. or less by spraying cooling water to an upper part of the cooling tower 2 and discharged through the upper part of the cooling tower 2. Here, a portion of cooling water discharged through the lower part of the cooling tower 2 was recycled into the cooling tower 2 and the remainder of the cooling water 8 was transferred to the equipment for removing a light byproduct 3.

Gas 7 discharged though the upper of the cooling tower 2 was absorbed into an organic solvent in an absorption tower (not shown), thereby being prepared into an organic solution. Water 8 discharged through a lower part of the cooling tower 2 was passed through the equipment for removing a light byproduct 3, i.e., a distill column (80° C. to 95° C.)

A light byproduct discharged to an upper part of the equipment for removing a light byproduct 3 was transferred to the equipment for treating waste water 6 via the transfer line 9, and water discharged from a lower part of the equipment for removing a light byproduct 3 was passed through the equipment for precipitating a heavy byproduct 4.

NaOH was fed into the equipment for precipitating a heavy byproduct 4 through an alkaline substance feed line 11 and pH 12 was adjusted.

A heavy byproduct precipitated after passing through the equipment for precipitating a heavy byproduct 4 was not discharged and was passed through the equipment for extracting steam 5, i.e., a boiler. Water discharged through a lower portion of the boiler was converted into 60% by weight of steam. Generated steam was supplied to the reactor for oxidation-dehydrogenating 1 via the transfer line 10.

The contents of light and heavy byproducts in water 8 discharged from the lower part of the cooling tower 2 were 924 ppm and 7705 ppm, respectively, as results analyzed through GC Mass. The contents of light and heavy byproducts in steam transferred to the reactor for oxidation-dehydrogenating 1 via the transfer line 10 were 0 ppm and 751 ppm, respectively. Accordingly, it was confirmed that supply of steam from which 100% by weight of the light byproduct and 90% by weight of the heavy byproduct were removed was carried out by treating water discharged through the lower part of the cooling tower 2 according to the present invention.

Example 1-2

An experiment was carried out in the same manner as in Example 1, except that the interior pH of the equipment for precipitating a heavy byproduct 4 was adjusted to 10.

The contents of light and heavy byproducts in water 8 discharged from a lower part of a cooling tower 2 were 924 ppm and 7705 ppm, respectively, as results analyzed through GC Mass. The contents of light and heavy byproducts in steam transferred to a reactor for oxidation-dehydrogenating 1 via a transfer line 10 were 0 ppm and 2650 ppm, respectively. Accordingly, it can be confirmed that 100% by weight of light byproduct was removed, but only 65% by weight of heavy byproduct was removed, by treating water discharged from the lower part of the cooling tower according to the present invention.

Therefore, it can be confirmed that, from Examples 1 and 1-2, the pH of the equipment precipitating a heavy byproduct affects removal of the heavy byproduct and the pH is preferably 11 or higher, more preferably 11 to 12.

Additional Example 1

An experiment was carried out in the same manner as in Example 1, except that a heavy product passed through an equipment for filtering (not shown) after passing through an equipment for precipitating a heavy byproduct, followed by passing through the equipment for extracting steam 5.

The contents of light and heavy byproducts in water 8 discharged through a lower part of the cooling tower were analyzed through GC Mass. As a result, the contents of the light and heavy byproducts were respectively 924 ppm and 7705 ppm. The contents of light and byproducts in steam supplied to the reactor for oxidation-dehydrogenating 1 via the transfer line 10 were respectively 0 ppm and 384 ppm. Accordingly, it can be confirmed that steam from which 100% by weight of the light byproduct and 95% by weight of the heavy byproduct had been removed was supplied by treating the water discharged from the lower part of the cooling tower according to the present invention.

Therefore, through the fact that a heavy byproduct treatment content was far increased, it was confirmed that it was more preferable to extract steam after precipitating the heavy byproduct precipitation and then filtering the same.

Examples 2 to 5, Contrast Example, and Comparative Example 1

Hereinafter, Examples 2 to 5, Contrast Example, and Comparative Example 1 were carried out to examine byproduct (carbonyl) content changes, per steam extraction ratio, included in steam extracted by the equipment for extracting steam 5 and determine whether the equipment was properly utilized.

Example 2

In Example 1, 60% by weight of steam extracted by the equipment for extracting steam 5 was supplied to the reactor for oxidation-dehydrogenating 1. The total content of byproducts included in the steam was confirmed to be 751 ppm through GC mass. The byproducts included a heavy byproduct and a small amount of a light byproduct. For reference, it may be analogized that the light byproduct was completely removed by the equipment for removing the light byproduct 3 of Example 1, but a portion of the light byproduct included in the heavy byproduct, etc. was melted out by operating the equipment for extracting steam 5 at high temperature and additionally analyzed.

Furthermore, a sample from generated gas at an outlet of the reactor for oxidation-dehydrogenating 1 was collected and a conversion rate, selectivity, and a yield of butadiene in the sample were calculated. As illustrated in #1 of FIG. 2, the conversion rate was 97.5%, selectivity was 95%, and the yield was 92.5%.

Contrast Example

An experiment was carried out in the same manner as in Example 2, except that fresh vapor was fed at a initial reaction step instead of recirculating steam. A conversion rate, selectivity, and a yield of butadiene in generated gas at the outlet of the reactor for oxidation-dehydrogenating 1 were calculated. As illustrated in #2 of FIG. 2, the conversion rate was 97.5%, the selectivity was 95%, and the yield was 92.5%, which were equal to the calculated values of Example 2. Accordingly, it can be confirmed that the effect of the steam recirculated according to the present invention is the same as that due to the use of the fresh.

Example 3

An experiment was carried out in the same manner as in Example 2, except that a steam extraction ratio through the equipment for extracting steam 5 was 50% by weight and converted steam was supplied to the reactor for oxidation-dehydrogenating 1. The total content of byproducts included in the steam was 918 ppm.

Example 4

An experiment was carried out in the same manner as in Example 2, except that a steam extraction ratio through the equipment for extracting steam 5 was 70% by weight and converted steam was supplied to the reactor for oxidation-dehydrogenating 1. The total content of byproducts included in the steam was 663 ppm.

Example 5

An experiment was carried out in the same manner as in Example 2, except that a steam extraction ratio through the equipment for extracting steam 5 was 80% by weight and converted steam was supplied to the reactor for oxidation-dehydrogenating 1. The total content of byproducts included in the steam was 496 ppm.

Comparative Example 1

An experiment was carried out in the same manner as in Example 2, except that a steam extraction ratio through the equipment for extracting steam 5 was 40% by weight and converted steam was supplied to the reactor for oxidation-dehydrogenating 1.

The total content of byproducts included in the steam was 1154 ppm. A sample was collected from generated gas at an outlet of the reactor for oxidation-dehydrogenating 1, and a conversion rate, selectivity and a yield of butadiene in the sample were calculated. As a result, the conversion rate was 92.5%, the selectivity was 90%, and the yield was 87.5%.

Therefore, it can be confirmed that, when the conversion rate, the selectivity, and the yield of the butadiene according to Comparative Example 1 are compared to those of the butadiene according to Example 2, a steam extraction ratio is preferably 50% by weight or more and the content of byproducts in converted steam is preferably less than 1154 ppm, 1000 ppm or less, 918 ppm or less, or 496 to 918 ppm.

As a result, it was confirmed that process efficiency can be increased by effectively treating water at a lower part discharged in the cooling step of the process of preparing conjugated diene, and converting steam to use in oxidative dehydrogenation according to embodiments of the present invention.

DESCRIPTION OF SYMBOLS

1: REACTOR FOR OXIDATION-DEHYDROGENATING, 2: COOLING EQUIPMENT (QUENCHER), 3: EQUIPMENT FOR REMOVING LIGHT BYPRODUCT, 4: EQUIPMENT FOR PRECIPITATING HEAVY BYPRODUCT, 5: EQUIPMENT FOR EXTRACTING STEAM, 6: EQUIPMENT FOR TREATING WASTE WATER, 7: GAS AT OUTLET OF COOLING EQUIPMENT, 8: LINE FOR TRANSFERRING WATER DISCHARGED THROUGH LOWER PART OF COOLING EQUIPMENT

The invention claimed is:

1. A method of preparing conjugated diene, wherein the method comprises:
    oxidatively-dehydrogenating a raw material gas comprising n-butene in an oxidative dehydrogenation reactor in the presence of a catalyst to form a generated gas comprising butadiene;
    contacting the generated gas with a cooling water to cool the generated gas to form a cooled generated gas and a discharged cooling water containing one or more byproducts;
    subjecting the discharged cooling water to a light byproduct removal process to remove a light byproduct comprising a carbonyl compound having a boiling point of 100° C. or less and a carbon number of 4, thereby producing a remaining discharged cooling water;
    subjecting the remaining discharged cooling water to a heavy byproduct precipitation process to precipitate a heavy byproduct comprising a carbonyl compound having a boiling point of 100° C. or less and a carbon number of 5 or 6, thereby producing a heavy byproduct precipitated cooling water, wherein the heavy byproduct precipitation process comprises adjusting a pH of the remaining discharged cooling water to 11 or more to precipitate the heavy byproduct;
    subjecting the heavy byproduct precipitated cooling water to a filtering process to remove the precipitated heavy byproduct, thereby producing a byproduct-removed cooling water;
    contacting the cooled generated gas with an absorption solvent to produce an organic solution;
    stripping the organic solution to obtain crude butadiene;
    converting the byproduct-removed cooling water into steam to form a converted steam; and
    recycling a portion of the converted steam to the oxidative dehydrogenation reactor, wherein an amount of the converted steam recycled to the oxidative dehydrogenation reactor is 50% by weight or more based on the weight of the discharged cooling water, and an amount of a carbonyl compound contained in the converted steam is 1000 ppm or less.

2. The method according to claim 1, wherein the light byproduct removal process is performed through distillation at a temperature range of from 80° C. to 95° C.

3. The method according to claim 1, wherein the heavy byproduct precipitation process is performed using a neutralization tank.

4. The method according to claim 1, wherein the contacting the generated gas with the cooling water is performed in a cooling equipment having an upper part and a lower part, the cooling water is introduced into the upper part, countercurrently contacting the generated gas that is introduced into the lower part to form a used cooling water.

5. The method according to claim 4, wherein a portion of the used cooling water is recirculated to the upper part of the cooling equipment.

6. The method according to claim 1, wherein a portion of the converted steam is not recycled to the oxidative dehydrogenation reactor and the precipitated heavy byproduct is incinerated.

* * * * *